US012691048B2

(12) United States Patent
Janssen et al.

(10) Patent No.: US 12,691,048 B2
(45) Date of Patent: Jul. 28, 2026

(54) TOPICAL COMPOSITION

(71) Applicant: DSM IP Assets B.V., Heerlen (NL)

(72) Inventors: Anne Janssen, Kaiseraugst (CH);
Gernot Ulrich Kunze, Kaiseraugst
(CH); Karina Radomsky, Kaiseraugst
(CH); Rolf Schuetz, Kaiseraugst (CH);
Jürgen Herbert Vollhardt, Kaiseraugst
(CH)

(73) Assignee: DSM IP ASSETS B.V., Maastricht
(NL)

( * ) Notice: Subject to any disclaimer, the term of this
patent is extended or adjusted under 35
U.S.C. 154(b) by 410 days.

(21) Appl. No.: 18/254,537

(22) PCT Filed: Nov. 26, 2021

(86) PCT No.: PCT/EP2021/083110
§ 371 (c)(1),
(2) Date: May 25, 2023

(87) PCT Pub. No.: WO2022/112476
PCT Pub. Date: Jun. 2, 2022

(65) Prior Publication Data
US 2024/0009102 A1        Jan. 11, 2024

(30) Foreign Application Priority Data

Nov. 27, 2020    (EP) .................................... 20210442

(51) Int. Cl.
*A61K 8/49* (2006.01)
*A61K 8/06* (2006.01)
*A61K 8/27* (2006.01)
*A61K 8/29* (2006.01)
*A61K 8/37* (2006.01)
*A61Q 17/04* (2006.01)

(52) U.S. Cl.
CPC ............ *A61K 8/4966* (2013.01); *A61K 8/062*
(2013.01); *A61K 8/27* (2013.01); *A61K 8/29*
(2013.01); *A61K 8/37* (2013.01); *A61Q 17/04*
(2013.01); *A61K 2800/30* (2013.01); *A61K*
*2800/621* (2013.01); *A61K 2800/624*
(2013.01); *A61K 2800/63* (2013.01)

(58) Field of Classification Search
None
See application file for complete search history.

(56) References Cited

U.S. PATENT DOCUMENTS

2011/0033400 A1    2/2011  Ehlis et al.
2013/0142737 A1*  6/2013  Schlifkeposchalko  .. A61K 8/35
                                                                        424/59

FOREIGN PATENT DOCUMENTS

| DE | 102017222739 A1 | 6/2019 |
|---|---|---|
| EP | 2092928 A1 | 8/2009 |
| EP | 3093005 A1 | 11/2016 |
| JP | 2011510053 A | 3/2011 |
| JP | 2011513205 A | 4/2011 |
| JP | 2014080377 A | 5/2014 |
| JP | 2015-178437 A | 10/2015 |
| JP | 2017095355 A | 6/2017 |
| JP | 2020111542 A | 7/2020 |
| WO | 2009077356 A2 | 6/2009 |
| WO | 2009092972 A2 | 7/2009 |
| WO | 2013055774 A1 | 4/2013 |
| WO | 2015139782 A1 | 9/2015 |
| WO | 2016002751 A1 | 6/2017 |
| WO | 2019115206 A1 | 6/2020 |
| WO | 2020054827 A1 | 8/2021 |

OTHER PUBLICATIONS

International Search Report for PCT/EP2021/083110, mailed Feb.
7, 2022, 3 pages.
Written Opinion of the ISA for PCT/EP2021/083110, mailed Feb. 7,
2022, 5 pages.
Database GNPD, MINTEL, "Urban Dust Free Sun Block SPF 41
PA++", www.gnpd.com, Aug. 14, 2017.

* cited by examiner

*Primary Examiner* — Nannette Holloman
(74) *Attorney, Agent, or Firm* — NIXON &
VANDERHYE P.C.

(57) ABSTRACT

The present invention relates to specific topical composi-
tions comprising bis-ethylhexyloxyphenol methoxyphenyl
triazine (BEMT), butyloctyl salicylate and at least one
inorganic UV-filter selected from titanium dioxide and zinc
oxide. Said compositions exhibit an appealing skin feel and
look.

20 Claims, No Drawings

TOPICAL COMPOSITION

This application is the U.S. national phase of International Application No. PCT/EP2021/083110 filed Nov. 26, 2021 which designated the U.S. and claims priority to EP 20210442.8 filed Nov. 27, 2020, the entire contents of each of which are hereby incorporated by reference.

The present invention relates to specific topical compositions comprising bis-ethylhexyloxyphenol methoxyphenyl triazine (BEMT), butyloctyl salicylate and at least one inorganic UV-filter selected from titanium dioxide and zinc oxide. Said compositions exhibit an appealing skin feel and look.

There is a increasing need for sunscreens having an sun protection factor (SPF) of 20 or more in order to provide effective protection against UV-radiation. At the same time, however, such sunscreens should still exhibit an appealing skin feel and look.

Inorganic UV-filters, i.e. micronized (often also called microfine) metal oxides such as titanium dioxide or zinc oxide are particularly useful in sunscreen applications due to their ability to increase the sun protection factor (SPF) of formulations over a broad UV range. In addition, these inorganic UV-filters are generally regarded as safe for cosmetic use and do not have the disadvantage of a tacky skin-feel as is the case with most organic UV filters. Nevertheless, there are still problems associated with the use of such inorganic UV-filters. In particular, the level of metal oxide powder necessary to achieve proper (and higher) SPF levels makes the product aesthetically unacceptable, i.e. there is a heavy and gritty feel and a white/blue residual on the skin.

Even though there has been no lack of attempts to develop efficient sunscreen compositions comprising inorganic UV-filters exhibiting a reduced skin whitening effect, this problem has not yet been solved to ultimate satisfaction, particularly in the case of preparations featuring a high sun protection factor.

It is therefore an ongoing need to develop novel sunscreen formulations comprising inorganic UV-filters which exhibit a reduced skin whitening effect, while having high sun protection factor (SPF 20 or more), which do not comprise 4-methoxyzimtsäureisoamylester (INCI: isoamyl p-methoxycinnamate, CAS No. 71617-10-2), 4-(dimethyl-amino)benzoesäure(2-ethylhexyl)ester (INCI: diethylamino hydroxybenzoyl hexyl benzoate; CAS No. 302776-68-7) and ethylhexyl 2-cyano-3,3-diphenylacrylate (INCI: octoc-rylene, CAS No. 6197-30-4).

The disadvantage of the use of the disclaimed UV filters, despite their approval by the approval authorities, is that they are not without controversy due to various reasons such as resulting in a downgrading in consumer magazines (e.g. eco-test) due to potential hormonal activity, discoloration of formulations or cloth staining.

Surprisingly, it has now be found, that the butyloctyl salicylate and/or bis-ethylhexyloxyphenol methoxyphenyl triazine are able to reduce the skin whitening effect of inorganic UV-filters in high SPF formulations which do not comprise Isoamyl p-Methoxycinnamate, Diethylamino hydroxybenzoyl hexyl benzoate and Octocrylene. The effect is particularly pronounced when BHB and BEMT are used in combination respectively the inorganic filter is a titanium dioxide, most preferably a double coated titanium dioxide comprising an inner silica and an outer dimethicone coating.

Thus, in a first embodiment, the present invention provides a topical sunscreen composition comprising bis-ethylhexyloxyphenol methoxyphenyl triazine (BEMT), butyloctyl salicylate (BHB) and at least one inorganic UV-filter selected from titanium dioxide and zinc oxide, with the proviso that the composition does not comprise (any of) isoamyl p-methoxycinnamate, diethylamino hydroxyben-zoyl hexyl benzoate and octocrylene.

Another subject matter of the invention is directed to a method of reducing the whitening effect caused by an inorganic UV-filter selected from titanium dioxide and/or zinc oxide in a topical composition comprising bis-ethyl-hexyloxyphenol methoxyphenyl triazine when applied to a surface such as in particular the skin, said method comprising the step of adding butyloctyl salicylate to said topical composition and optionally appreciating the effect.

It is preferred, that the composition does not comprise (any of) isoamyl p-methoxycinnamate, diethylamino hydroxybenzoyl hexyl benzoate and octocrylene In a further embodiment the invention relates to the use of butyloctyl salicylate to reduce the (skin) whitening effect of an inorganic UV-filter selected from titanium dioxide and zinc oxide, in particular when incorporated into a topical composition in combination with bis-ethylhexyloxyphenol methoxyphenyl triazine. It is preferred, that composition does not comprise (any of) isoamyl p-methoxycinnamate, diethylamino hydroxybenzoyl hexyl benzoate and octoc-rylene.

The invention also relates to the use of butyloctyl salicy-late in combination with bis-ethylhexyloxyphenol methoxy-phenyl triazine to reduce the (skin) whitening effect of an inorganic UV-filter selected from titanium dioxide and zinc oxide.

The term 'topical' as used herein is understood to mean external application to keratinous substances, which are in particular the skin, scalp, eyelashes, eyebrows, nails, mucous membranes and hair, preferably the skin.

Bis-Ethylhexyloxyphenol methoxyphenyl triazine (also referred to herein as BEMT) is also known as 2,4-bis{[4-(2-ethylhexyloxy)-2-hydroxy]phenyl}-6-(4-methoxyphe-nyl)-1,3,5-triazine (chemical name) or bemotrizinol (INN) (CAS Number 187393-00-6). BEMT acts as a broad-spec-trum UV filter absorbing UVB as well as UVA rays. It has two absorption peaks, 310 and 340 nm. BEMT is suggested for use in sun, day care, alphabetic products such as BB cream, whitening products, color cosmetics.

In all embodiments of the present invention, the amount of BEMT in the topical compositions according to the present invention is advantageously selected in the range from 0.4 to 10 wt.-%., preferably in the range from 0.4 to 9 wt.-%, 0.4 to 8 wt.-%, 0.4 to 7 wt.-%, 0.4 to 6 wt.-%, 0.4 to 5 wt.-%, 0.4 to 4 wt.-%, 0.4 to 3 wt.-%, 0.5 to 3 wt.-%, 0.8 to 9 wt.-%, 0.8 to 8 wt.-%, 0.8 to 7 wt.-%, 0.8 to 6 wt.-%, 0.8 to 5 wt.-%, 0.8 to 4 wt.-%, 0.8 to 3 wt.-%, such as for instance in the range from 1 to 5 wt.-%, from 1 to 3 wt.-%, from 2 to 5 wt.-% or from 2 to 4 wt.-%, based on the total weight of the composition.

Butyloctyl salicylate (also referred to herein as BHB) is also known as 2-hydroxy-benzoic acid 2-butyloctyl ester (CAS Number. 190085-41-7). BHB generally acts as solu-bilizer for some commonly used UV-filters like oxybenzone or avobenzone and it can also help to increase the SPF rating of sunscreens.

In all embodiments of the present invention, the amount of BHB in the in the topical compositions according to the present invention is advantageously selected in the range from 0.5 to 10 wt.-%, preferably in the range from 0.5 to 9 wt.-%, 0.5 to 8 wt.-%, 0.5 to 7 wt.-%, 0.5 to 6 wt.-%, 0.5 to 5 wt.-%, 1 to 9 wt.-%, 1 to 8 wt.-%, 1 to 7 wt.-%, 1 to 6 wt.-%, 2 to 9 wt.-%, 2 to 8 wt.-%, 2 to 6 wt.-%, such as for instance in the range from 2.5 to 5 wt.-%, from 2 to 3 wt. %, or from 2 to 5 wt.-%, based on the total weight of the composition.

The term 'inorganic UV-filter' as used herein refers to any metal oxide particles having a particle size which allows the absorption of UV-light and are thus useful for incorporation into sunscreen compositions as UV filters. Such inorganic UV-filters are well known to a person skilled in the art and are often referred to as micronized or microfine titanium dioxide or zinc oxide.

The particle size of such inorganic UV-filter is not particularly limited. In general, suitable (primary) particle sizes for an efficient UV-light absorption are in the range of 2 to 200 nm.

If not indicated otherwise, the particles sizes as given herein refer to the mean number-based particle size distribution Dn50 (also known as Dn0.5) as determined by laser diffraction e.g. with a Horiba particle size distribution analyzer LA-960 or a Malvern Mastersizer 2000 (ISO 13320: 2009).

In all embodiments of the present invention, the amount of the inorganic UV-filter in the topical composition is preferably selected in the range from 0.5 to 25 wt.-%, more preferably in the range from 1 to 20 wt.-%, and most preferably in the range from 2 to 15 wt.-%, based on the total weight of the composition. Further suitable amounts are selected in the range from 1 to 7 wt.-%, 2 to 7 wt.-%, 3 to 7 wt.-%, 1 to 6 wt.-%, 2 to 6 wt.-% and 3 to 6 wt.-%.

Even more advantageously, the amount of the inorganic titanium dioxide UV-filter in the topical compositions according to the present invention is selected in the range of 0.5 to 15 wt.-%, preferably in the range of 1 to 15 wt.-%, more preferably in the range of 2 to 10 wt.-%, most preferably in the range of 2 to 6 wt.-% or 3 to 6 wt.-%, based on the total weight of the composition.

Even more advantageously, the amount of the inorganic zinc oxide UV-filter in the topical compositions according to the present invention is selected in the range of 0.5 to 25 wt. %, preferably in the range of 1 to 15 wt.-%, more preferably in the range of 2 to 15 wt.-%, most preferably in the range of 5 to 15 wt.-% or 7.5 to 15 wt.-%, based on the total weight of the composition.

According to the invention, it is advantageous that the inorganic UV-filters are surface-coated. The surface coating may comprise providing the metal oxide particles with a thin hydrophilic or hydrophobic inorganic or organic layer by methods known per se. According the present invention the different surface coatings can also comprise water. As a result of the surface treatment, the metal oxide is given a hydrophilic, amphiphilic or hydrophobic character.

Examples of inorganic surface coatings which are suitable for the purposes of the instant invention comprise aluminum oxide ($Al_2O_3$), aluminum hydroxide $Al(OH)_3$, aluminum oxide hydrate (also: Alumina, CAS-No.: 1333-84-2), sodium hexametaphosphate ($NaPO_3$)e, sodium meta-phosphate ($NaPO_3$)e, silicon dioxide ($SiO_2$) (also: Silica, CAS-No.: 7631-86-9), and iron oxide ($Fe_2O_3$). These inorganic surface coatings can be present on their own, in combination and/or in combination with organic coating materials, in particular as outlined below.

Examples of organic surface coatings which are suitable for use in the present invention include vegetable or animal aluminum stearate, fatty acids such as stearic acid and lauric acid, dimethylpoysiloxane (also: dimethicone), methylpolysiloxane (methicone), simethicone, triethoxycaprylylsilane, octyttrimethoxysilane and cetyl phosphates such as potassium cetyl phosphate as well as any mixtures thereof. These organic surface coatings can be present on their own, in combination and/or in combination with inorganic coating materials.

The crystalline form of the titanium dioxide may be of any crystal or amorphous type. For example, titanium dioxide may be any type of amorphous, rutil, anastase, brookite or a mixture thereof. Preferably, in all embodiments of the present invention, the crystalline form of the titanium dioxide is rutil.

It is furthermore preferred that the zinc oxide is a white powder consisting of zinc oxide present as wurtzite crystal structures.

Titanium dioxide particles for use according to the present invention and pre-dispersions of titanium dioxide particles are e.g. available as PARSOL® TX (INCI: titanium dioxide, silica, dimethicone) at DSM Nutritional Products Ltd., Micro Titanium dioxide MT-01 at Tayca or TTO-55(C) at Ishihara Sangyo Kaisha. Also suitable is double coated titanium dioxide having an inner alumina coating and an outer simethicone coating e.g. commercially available as Eusolex T-2000 at EMD chemicals Inc./Rona.

Zinc oxide particles for use according to the present invention and pre-dispersions of zinc oxide particles are e.g. available from BASF as Z-Cote or Z-Cote HP1 (2% dimethicone coating), from Tayca as MZ-505S (5% methicone coating), or from DSM Nutritional Products Ltd as PARSOL® ZX (2-3.5% triethoxycapryylsilane coating).

In a particular embodiment the topical compositions according to the present invention comprise as inorganic UV-filter either a double coated titanium dioxide and/or a coated zinc oxide, most preferably in the absence of any further microfine metal oxides.

Most preferably in all embodiments according to the present invention the titanium dioxide is a double coated titanium dioxide, even more preferably a double coated titanium dioxide having an inner silica and an outer organic coating.

Preferably, the inner silica coating layer of the double coated titanium dioxide consists of a minimum of 0.5 wt.-% of inorganic silica (based on titanium dioxide). More, preferably the inner coating layer consists of 0.5 wt.-% to 50 wt.-%, most preferably of 1 wt.-% to 20 wt.-% of inorganic silica (based on titanium dioxide).

The outer coating of the double coated titanium dioxide is preferably selected from the class of organic coatings such e.g. silicone oils (e.g. simethicones, methicones, dimethicones, polysilicone-15), alkyl silanes (e.g. octyl tri(m) ethoxy silane), olefinic acids (e.g. stearic acid), or polyols (e.g. glycerol) and can be applied to the titanium dioxide particle by methods known to a person skilled in the art e.g. described in FI57124. Preferably the outer coating is selected from the group consisting of simethicone, methicone, dimethicone, polysilicones-15, stearic acid and octyl trimethoxy silane. Most preferably the outer coating is dimethicone. Even more preferably, the amount of the outer coating layer is at least 0.25 wt.-% based on the titanium dioxide. Preferably the amount of the outer coating is selected in the range of 0.5 wt.-% to 50 wt.-%, most preferably in the range of 0.5 wt.-% to 10 wt.-%, based on the titanium dioxide.

In all embodiments of the present invention, the double coated titanium dioxide according to the present invention preferably has a titanium dioxide content selected in the range of 70-95 wt.-% and a silicon dioxide content selected in the range of 5-20 wt.-%, such as preferable a titanium dioxide content selected in the range of 80-90 wt.-% and a silicon dioxide content selected in the range of 10 to 15 wt.-%, with the proviso that the total content of titanium dioxide and silicone dioxide is selected in the range of 90-100 wt.-%.

Preferably, the double coated titanium dioxide has a mean primary particle size in the range from 2 to 100 nm, more preferably in the range of 5 to 50 nm, most preferably in the range of 10 to 25 nm and a secondary particle size between 0.025 and 1 μm, such as preferably between 0.05 and 0.075 μm.

Particularly suitable double coated titanium dioxide according to the present invention contains a rutil-type titanium dioxide ($TiO_2$) core with a double coating of silica (inner coating) and dimethicone (outer coating) and has titanium dioxide content of at least 75 wt. %, preferably in the range from 82-87 wt.-% and a silicon dioxide content of at least 10 wt.-%, preferably in the range from 10.5 to 14.5 wt.-%, and a mean particle size distribution $D_n50$ of 25 to 100 nm, preferably 40 to 80 nm (analysed by Laser diffraction measurements with a Malvern Mastersizer 2000), which double coated titanium dioxide is e.g. commercially available as PARSOL® TX (INCI: titanium dioxide, silica, dimethicone) at DSM nutritional products Ltd.

Most preferably, in all embodiments according to the present invention, the zinc oxide is coated with triethoxy-capryylsilane. Most preferably, the zinc oxide is a white powder consisting of zinc oxide present as wurtzite crystal structures, coated with triethoxycaprytylsilane, which has a zinc oxide content of 96-98%, a triethoxycapryylsilane content of 2-3.5% and a mean particle size of 90 to 130 nm (analysed by Laser diffraction measurements with a Malvern Mastersizer 2000).

In a particular advantageous embodiment, the compositions according to the present invention do not comprise ethyihexyl salicylate. Even more preferable, the compositions according to the present invention solely comprise bis-ethyihexyloxyphenol methoxyphenyl triazine, butyloctyl salicylate and at least one inorganic UV-filter selected from titanium dioxide and zinc oxide as UV absorbers, i.e. no further UV-filters are present in the composition.

As the topical compositions according to the invention are intended for topical application, it is well understood that they comprise a physiologically acceptable medium, i.e. a medium compatible with keratinous substances, such as the skin, mucous membranes, and keratinous fibres. In particular, the physiologically acceptable medium is a cosmetically acceptable carrier.

The term 'cosmetically acceptable carrier' as used herein refers to all carriers and/or excipients and/or diluents conventionally used in topical cosmetic compositions such as in particular in skin care preparations.

The exact amount of carrier will depend upon the actual level of the UV filters and any other optional ingredients that one of ordinary skill in the art would classify as distinct from the carrier (e.g., other active ingredients).

In an advantageous embodiment, the topical compositions according to the present invention comprise from 50% to 99%, preferably from 60% to 98%, more preferably from 70% to 98%, such as in particular from 80% to 95% of a carrier, based on the total weight of the topical composition.

In a particular advantageous embodiment, the carrier consists furthermore of at least 30 wt. %, more preferably of at least 40 wt.-%, most preferably of at least 45 wt.-% of water, such as in particular of 50 to 90 wt.-% of water.

In particular, the topical composition according to the present invention are cosmetic or pharmaceutical compositions, preferably cosmetic (non-therapeutic) compositions.

In one embodiment, the topical compositions according to the present invention are applied to mammalian keratinous tissue such as in particular to human skin or the human scalp and hair.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4th edition, 1992.

Preferred topical compositions according to the invention are skin care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of decorative preparations are, in particular, lipsticks, eye shadows, mascaras, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or antimicrobial (antibacterial or antifungal) preparations without being limited thereto.

In a particular embodiment, the topical compositions according to the invention are light-protective preparations (sun care products, sunscreens), such as sun protection milks, sun protection lotions, sun protection creams, sun protection oils, sun blocks or tropical's or day care creams with a SPF (sun protection factor). Of particular interest are sun protection creams, sun protection lotions and sun protection milks.

The compositions of the invention (including the carrier) may comprise conventional adjuvants and additives, such as preservatives/antioxidants, fatty substances/oils, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing agents, as well as agents to improve elasticity and skin barrier and/or further UV-filter substances and carriers and/or excipients or diluents conventionally used in topical compositions.

If nothing else is stated, the excipients, additives, diluents, etc. mentioned in the following are suitable for topical compositions according to the present invention. The necessary amounts of the cosmetic and dermatological adjuvants and additives can, based on the desired product, easily be determined by the skilled person.

The additional ingredients can either be added to the oily phase, the aqueous phase or separately as deemed appropriate. The mode of addition can easily be adapted by a person skilled in the art.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

Preferred topical compositions in all embodiments of the present invention are emulsions containing an oily phase and an aqueous phase such as in particular an O/W, W/O, Si/W, W/Si, O/W/O, W/O/W multiple or a pickering emulsions. The amount of the oily phase (i.e. the phase containing all oils and fats) present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the composition.

According to one even more preferred embodiment, the topical compositions according to the present invention as outlined herein are O/W emulsions comprising an oily phase dispersed in an aqueous phase in the presence of an 0/W emulsifier. The preparation of such O/W emulsions is well known to a person skilled in the art and illustrated in the examples.

In one advantageous embodiment, the 0/W emulsifier is a phosphate ester emulsifier. Among the preferred phosphate ester emulsifier are C8-10 Alkyl Ethyl Phosphate, C9-15 Alkyl Phosphate, Ceteareth-2 Phosphate, Ceteareth-5 Phosphate, Ceteth-8 Phosphate, Ceteth-10 Phosphate, Cetyl Phosphate, C6-10 Pareth-4 Phosphate, C12-15 Pareth-2 Phosphate, C12-15 Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate. A particular phosphate ester emulsifier according to the invention is potassium cetyl phosphate e.g. commercially available as Amphisol® K at DSM Nutritional Products Ltd Kaiseraugst.

Further suitable O/W emulsifiers according to the present invention encompass PEG 30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Poyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, glyceryistearatcitrate, glyceryistearate (self-emulsifying), stearic acid, salts of stearic acid, poyglyceryl-3-methylgycosedistearate. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Poystearate and Hydrated Polyisobuten. Furthermore, one or more synthetic polymers may be used as an emulsifier. For example, PVP eicosene copolymer, acrylates/C10-30 alkyl acrylate crosspolymer, acrylates/steareth-20 methacrylate copolymer, PEG-22/dodecyl glycol copolymer, PEG-45/dodecyl glycol copolymer, and mixtures thereof.

Another particular suitable class of O/W emulsifiers are non-ionic self-emulsifying system derived from olive oil e.g. known as (INCI Name) cetearyl olivate and sorbitan olivate (Chemical Composition: sorbitan ester and cetearyl ester of olive oil fatty acids) sold under the tradename OLIVEM 1000.

Further suitable are commercially available polymeric emulsifiers such as hydrophobically modified polyacrylic acid such as Acrylates/C10-30 Alkyl Acrylate Crosspolymers which are commercially available under the tradename Pemulen® TR-1 and TR-2 by Noveon.

Another class of particularly suitable emulsifiers are polyglycerol esters or diesters of fatty acids also called polyglyceryl ester/diester (i.e. a polymer in which fatty acid(s) is/are bound by esterification with polyglycerine), such as e.g. commercially available at Evonik as Isolan GPS [INCI Name Poygyceryl-4 Diisostearate/Polyhydroxystearate/Sebacate (i.e. diester of a mixture of isostearic, polyhydroxystearic and sebacic acids with Poygycerin-4)] or Dehymuls PGPH available at Cognis (INCI Poygyceryl-2 Dipolyhydroxystearate).

Also suitable are poyalkylengycolether such as Brij 72 (Polyoxyethylen(2)stearylether) or Brij 721 (Polyoxyethylene (21) Stearyl Ether e.g. available at Croda.

Particularly advantageous O/W emulsifiers according to the present invention are one or more of Poygyceryl-3 Methylglucose Distearate, Lauryl Glucoside (and) Poygyceryl-2 Dipolyhydroxystearate, Glyceryl Sterate Citrate, Sodium Cetearyl Sulfate, Cetearyl Glucoside; Poygyceryl-6 Stearate (and) Poygyceryl-6 Behenate, Cetearyl Olivate (and) Sorbitan Olivate, Arachidyl Alcohol (and) Behenyl Alcohol (and) Arachidyl Glucosides, Cetearyl Alcohol (and) Coco-Glucoside, Coco-Glucoside (and) Coconut Alcohol, PEG-100 Stearate (and) Glyceryl Stearate, Sodium Stearoyl Glutamate, Steareth-20, Steareth-21, Steareth-25, Steareth-2, Ceteareth-25 and Ceteareth-6 (all listed by their INCI names).

It is particularly preferred in accordance with the invention if the composition comprises potassium cetyl phosphate as emulsifier.

The at least one O/W respectively Si/W emulsifier is preferably used in an amount of 0.5 to 10 wt. % such as in particular in the range of 0.5 to 5 wt.-% such as most in particular in the range of 0.5 to 4 wt.-%, based on the total weight of the composition.

Suitable W/O- or W/Si-emulsifiers according to the present invention are poygyceryl-2-dipoyhydroxystearat, PEG-30 dipolyhydroxystearat, cetyl dimethicone copolyol, poygyceryl-3 diisostearate polyglycerol esters of oleidisostearic acid, poygyceryl-6 hexaricinolate, poygyceryl-4-oleate, poygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Poygyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

It is of advantage in accordance with the invention if the compositions of the invention are, also free from polyethylene glycol, polyethylene glycol ethers, and polyethylene glycol esters (so-called PEG derivatives).

The topical compositions according to the present invention furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 7 wt.-%, such as most in particular in the range of 1 to 5 wt.-%, based on the total weight of the composition. Particular suitable co-surfactants are selected from the list of alkyl alcohols such as cetyl alcohol (Lorol C16, Lanette 16), cetearyl alcohol (Lanette 0), stearyl alcohol (Lanette 18), behenyl alcohol (Lanette 22), gyceryl stearate, glyceryl myristate (Estol 3650), hydrogenated coco-glycerides (Lipocire Na10) as well as mixtures thereof.

In all embodiments of the present invention, R is particular advantageous if the composition also comprises cetyl alcohol, stearyl alcohol and/or glycerylstearate, preferably stearyl alcohol.

Advantageous embodiments of the composition of the present invention also include those wherein the composition comprises one or more oils selected from butylene glycol dicaprylate/dicaprate, phenethyl benzoate, $C_{12}$-$C_{15}$ alkyl benzoate, dibutyl adipate, diisopropyl sebacates, dicaprylyl carbonate, di-$C_{12-13}$ alkyl tartrates, butyloctyl salicylates, diethylhexyl syringylidene malonates, hydrogenated castor oil dimerates, triheptanoin, $C_{12-13}$ alkyl lactates, C16-17 alkyl benzoates, propylheptyl caprylates, caprylic/capric triglycerides, diethylhexyl 2,6-naphthalates, octyldodecanol, ethylhexyl cocoates. Preferably, the composition according to the present invention comprises as oil(s) dibutyl adipate, dicaprytyl carbonate, $C_{12}$-$C_{15}$ alkylbenzoate, caprytyl carbonate, capric/caprylic triglyceride as well as mixtures thereof, most preferably dibutyl adipate, dicaprylyl carbonate and/or $C_{12}$-$C_{15}$ alkyl benzoate.

In a still further advantageous aspect of the invention, the topical compositions of the present invention further comprise a preservative and/or a preservative booster, preferably selected from the group consisting of ethanol, phenoxyethanol, ethylhexylglycerin, hexylglycerin, glyceryl caprylate, 1,2-pentanediol, 1,2-hexanediol, 1,2-octanediol (caprytyl glycol), 1,2-decanediol, 2-methyl-1,3-propanediol, propanediol, propylene glycol, p-hydroxyacetophenone as well as mixtures thereof, most preferably selected from the group of phenoxyethanol and ethylhexylgycerine as well as mixtures thereof. When present, the preservative respectively the preservative booster is preferably used in an amount of 0.01 to 2 wt. %, more preferably in an amount of 0.05 to 1.5 wt.-%, most preferably in an amount of 0.1 to 1.0 wt.-%, based on the total weight of the composition.

It is advantageous in accordance with the invention if the preparation comprises one or more alkanediols from the group 1,2-pentanediol, 1,2-hexanediol, 1,2-octanediol, 1,2-decanediol, 2-methyl-1,3-propanediol.

It is further advantageous in accordance with the invention if the composition of the invention comprises ethanol, p-hydroxyacetophenone phenoxyethanol and/or ethylhexylglycerin.

In another advantageous aspect, the topical compositions according to the present invention are free of any parabenes, benzethoniumchlorid, piroctone olamine, lauroylarginat, methylisothiazolinon, chlormethylisothiazolinon, bronopol, benzalkoniumchloride, formaldehyd releasing compounds, salicylic acid, triclosan, DMDM hydantoin, chlorphenesin and IPBC (lodopropinylbutyl carbamate).

The topical compositions according to the invention may further contain one or more emollients which soothe and soften the skin. As an example, the emollient may be silicone (dimethicone, cyclomethicone), vegetable oils (grape seed, sesame seed, jojoba, etc.), butters (cocoa butter, shea butter), and petrolatum derivatives (petroleum jelly, mineral oil).

In another aspect, the topical composition of the invention may comprise one or more fragrances selected from limonene, citral, linalool, alpha-isomethylionone, geraniol, citronellol, 2-isobutyl-4-hydroxy-4-methyttetrahydropyran, 2-tert-pentylcyclohexyl acetate, 3-methyl-5-phenyl-1-pentanol, 7-acetyl-1,1,3,4,4,6-hexamethyttetralin, adipic diester, cinnamal, amyl salicylate, alpha-amylcinnamaldehyde, alpha-methylionone, butylphenylmethylpropional, cinnamal, amylcinnamyl alcohol, anise alcohol, benzoin, benzyl alcohol, benzyl benzoate, benzyl cinnamate, benzyl salicylate, bergamot oil, bitter orange oil, butylphenylmethylpropional, cardamom oil, cedrol, cinnamal, cinnamyl alcohol, citronellyl methyicrotonate, citrus oil, coumarin, diethyl succinate, ethyllinalool, eugenol, Evemia furfuracea extract, Evemia prunastri extract, famesol, guaiacwood oil, hexylcinnamal, hexyl salicylate, hydroxycitronellal, lavender oil, lemon oil, linalyl acetate, mandarin oil, menthyl PCA, methyl heptenone, nutmeg oil, rosemary oil, sweet orange oil, terpineol, tonkabean oil, Methyl citrate, vanillin.

The composition of the invention may advantageously comprise moisturizers. Moisturizers are compounds or mixtures of compounds which give cosmetic compositions the quality, after application to or distribution on the skin surface, of reducing the loss of moisture of the stratum comeum (also called transepidermal water loss (TEWL)) and/or of positively influencing the hydration of the stratum comeum.

Non-limiting examples of advantageous moisturizers for use in the present invention include glycerol, lactic acid and/or lactates, especially sodium lactate, butylene glycol, propylene glycol, biosaccharide gum-1, Glycine soya, ethylhexyloxyglycerol, pyrrolidonecarboxylic acid, and urea. Of further advantage, in particular, is the use of polymeric moisturizers from the group of the polysaccharides which are water-soluble and/or swellable in water and/or gellable with the aid of water. Especially advantageous, for example, are hyaluronic acid, chitosan and/or a fucose-rich polysaccharide which is registered in Chemical Abstracts under the registry number 178463-23-5 and is available, for example, under the Fucoge191000 name from the company SOLABIA S.A. Moisturizers may also be used advantageously as active antiwrinkle ingredients for protection from changes to the skin of the kind occurring in skin aging, for example.

The cosmetic compositions of the invention may further comprise advantageously, although not mandatorily, fillers which have the effect, for example, of further improving the sensorial and cosmetic properties of the formulations and evoking or intensifying a velvety or silky skin sensation, for example. Advantageous fillers in the sense of the present invention are starch and starch derivatives (such as tapioca starch, distarch phosphate, aluminum or sodium starch octenylsuccinate, and the like, for example), VaNance pigments which have neither primarily UV filter effect nor coloring effect (such as Valvance Touch 210 or 250 for example) and/or Aerosils® (CAS No. 7631-86-9) and/or talc and/or polyethylene, nylon, and silica dimethyl silylate.

The water phase of the compositions of the invention may advantageously comprise customary cosmetic auxiliaries, such as, for example, alcohols, particularly those of low C number, preferably ethanol and/or isopropanol, or polyols of low C number, and also ethers thereof, preferably propylene glycol, glycerol, electrolytes, self-tanning agents, and also, in particular, one or more thickeners, which may be advantageously selected from the group of silicon dioxide, aluminum silicates, polysaccharides and/or derivatives thereof, e.g., hyaluronic acid, xanthan gum, hydroxypropylmethylcellulose, particularly advantageously from the group of polyacrylates, preferably a polyacrylate from the group referred to as Carbopols, examples being carbopols of types 980, 981, 1382, 2984, and 5984, in each case individually or in combination. Further thickeners advantageous in accordance with the invention are those having the INCI designation Acrylates/C10-30 Alkyl Acrylate Crosspolymer (e.g., Pemulen TR 1, Pemulen TR 2, Carbopol 1328 from NOVEON) and also Aristofiex AVC (INCI: Ammonium AcryloyldimethyltaurateNP Copolymer) as well as Simugel NS (INCI: Hydroxyethyl Acrylate/Sodium Acryloyldimethyl Taurate Copolymer 8 Squalane 8 Polysorbate 60).

It is preferred in accordance with the invention if the composition comprises xanthan gum, crosslinked acrylate/C10-C30 alkyl acrylate polymer, hydroxyethyl acrylate/sodium acryloyldimethyl taurate copolymer, and/or vinylpyrrolidone/hexadecene copolymer, preferably xanthan gum and/or hydroxyethyl acrylate/sodium acryloyldimethyl Taurate.

Besides the bis-ethyihexyloxyphenol methoxyphenyl triazine (BEMT) BHB and the inorganic UV-filter, one or more further UV filters may be present in the topical composition according to the present invention. These UV filters are in particular (INCI names) methylene bis-benzotriazoyl tetramethylbutyiphenol, tris-biphenyl triazine, phenylbenzimidazol sulfonic acid, dimethicodiethyl benzalmalonate, 4-methylbenzylidene camphor, ethylhexyl salicylate, homosalate, ethylhexyl triazone, diethyihexyl butamido triazone, butyl methoxydibenzoyl methane, disodium phenyl dibenzimidazole tetrasulfonate and oxybenzone without being limited thereto.

In an advantageous aspect of the invention, however, the topical compositions according to the present invention furthermore do not contain (i.e. are also free of) 3-(4-methylbenzylidene)camphor (INCI: 4-methylbenzylidene camphor), 2-hydroxy-4-methoxybenzophenone (INCI: Oxybenzone) and/or ethylhexyl methoxycinnamate.

The topical compositions of the invention manage with a surprisingly small total amount of UV filters.

In another aspect, the composition may have an SPF of at least 18.2, for example at least 20, preferably at least 30.

Advantageously in accordance with the invention, the composition of the invention comprises film formers. Film formers in the sense of the present invention are substances of various constitutions, and are characterized by the following properties: When a film former is dissolved in water or other suitable solvents, and when the solution is then applied to the skin, the film former, following evaporation of the solvent, forms a film which serves essentially to fix the photofilters on the skin and to so increase the water resistance of the product.

It is especially advantageous to select the film formers from the group of the polymers based on polyvinylpyrrolidone (PVP) Particular preference is given to copolymers of vinylpyrrolidone, as for example the PVP hexadecene copolymer and the PVP eicosene copolymer, which are available under the trade names Antaron V216 and Antaron V220 from GAF Chemicals Corporation.

Likewise advantageous are further polymeric film formers, such as, for example, sodium polystyrene sulfonate, which is available under the trade name Flexan 130 from National Starch and Chemical Corp., and/or polyisobutene, available from Rewo under the trade name Rewopal PIB1000. Examples of further suitable polymers are polyacrylamides (Seppigel 305), polyvinyl alcohols, PVP, PVPNA copolymers, polyglycols, acrylate/octylacrylamide copolymer (Dermacryl 79) Likewise advantageous is the use of hydrogenated castor oil dimer dilinoleate (CAS 646054-62-8, INCI Hydrogenated Castor Oil Dimer Dilinoleate), which can be acquired from Kokyu Alcohol Kogyo under the name Risocast DA-H, or else PPG-3 benzyl ether myristate (CAS 403517-45-3), which can be acquired under trade name Crodamol STS from Croda Chemicals.

The topical compositions according to the invention in general have a pH in the range of 3 to 10, preferably a pH in the range of 4 to 8 and most preferably a pH in the range of 4 to 7. The pH can easily be adjusted as desired with suitable acids such as e.g. citric acid or bases such as NaOH according to standard methods in the art.

In accordance with the invention is the use of the composition of the invention for protection from skin aging (especially for protection from UV-induced skin aging) and also as a sun protection composition.

Finally, a subject-matter of the invention is a method for the cosmetic treatment of keratinous substances such as in particular the skin, wherein a composition as defined herein is applied to the said keratinous substances such as in particular to the skin. The method is in particular suitable to protect the skin against the adverse effects of UV-radiation such as in particular sun-burn and/or photoageing while reducing the skin whitening effect of an inorganic UV-filter selected from the group of titanium dioxide and/or zinc oxide.

The following examples are provided to further illustrate the compositions and effects of the present invention. These examples are illustrative only and are not intended to limit the scope of the invention in any way.

Experimental Part

1. EXAMPLE 1

Cream formulations as outlined in table 1a have been prepared. Afterwards, cream has been applied on Leneta cards in a film thickness of 60 μm by using a rakel and a spreading speed of 10 mm/sec. with the following procedure: Afterwards, the whitening has been assessed by measuring the L value (for every formulation 4 cards, on each card 3 spots are measured: 12 values/formulation). Explanation of L value: the higher the value, the more white/bluish is the film.

TABLE 1a

| Phase | trade name | INCI | Ref-1.1 | Ref-1.2 | Inv-1.1 | Inv-1.2 |
|---|---|---|---|---|---|---|
| | | Formulations | | | | |
| A | Water Dem. | Aqua | Ad 100 | Ad 100 | Ad 100 | Ad 100 |
| A | Keltrol CG-T | Xanthan Gum | 0.25 | 0.25 | 0.25 | 0.25 |
| A | 1,3 Butylene Glycol | Butylene Glycol | 3.00 | 3.00 | 3.00 | 3.00 |
| A | Edeta BD | Disodium EDTA; | 0.10 | 0.10 | 0.10 | 0.10 |
| B | AMPHISOL ® K | Potassium Cetyl Phosphate | 2.50 | 2.50 | 2.50 | 2.50 |
| B | Lanette 18 | Stearyl alcohol | 2.50 | 2.50 | 2.50 | 2.50 |
| B | Finsolv TN | C12-15 Alkyl Benzoate | 15.00 | 15.00 | 15.00 | 15.00 |
| B | Cetiol CC | Dicaprylyl Carbonate | 10.00 | 10.00 | 5.00 | 5.00 |
| B | Cetiol B | Dibutyl Adipate | 3.00 | 3.00 | 3.00 | 3.00 |
| B | PARSOL ® Shield | Bis-Ethylhexyloxyphenol Methoxyphenyl Triazine (BEMT) | 3.00 | 3.00 | 3.00 | 3.00 |
| B | PARSOL ® TX | Titanium Dioxide, Silica, Dimethicone | 5.00 | | 5.00 | |
| B | PARSOL ® ZX | Zinc Oxide, Triethoxycaprilylsilane | | 15.00 | | 15 |
| B | Hallbrite BHB | Butyloctyl Salicylate | | | 5.00 | 5.00 |
| B | Euxyl PE 9010 | Phenoxyethanol; Ethylhexylglycerin | 1.00 | 1.00 | 1.00 | 1.00 |
| B | Sepinov EMT 10 | Hydroxyethyl Acrylate/ Sodium Acryloyldimethyl Taurate Copolymer | 0.40 | 0.40 | 0.40 | 0.40 |
| | SPF (calcuated)* | | 16.9 | 21.2 | 18.2 | 21.6 |

*DSM sunscreen optimizer ™

TABLE 1b

| Results of the whitening test | | |
|---|---|---|
| | Ref-1 | Inv-1 |
| Average L value before washing | 34.7 | 33.6 |
| Reduction of whitening vs. reference | — | −3.2% |

As can be retrieved from table 2, the addition of BHB reduced the whitening of a sunscreen comprising BEMT and an inorganic UV filter.

2. EXAMPLE 2

The formulations (O/W emulsions) as outlined in table 2 have been prepared according to standard methods in the art. Then the soaping effect on LENETA black cards has been tested according to the method as outlined below:

Apply 300 mg of cream on LENETA black card
cream is spread by in house developed spreading device (speed: 10 mm/s) using a 90 mm spreading knife for homogenous film thickness
LAB is measured by Minolta Chroma Meter CR-300 immediately after application, 3 measuring spots on each card (4 cards were prepared)
average L value is calculated and compared

TABLE 2

| Phase | trade name | INCI | Ref 2.1 | Inv-2.1 2 | Ref.2.2 |
|---|---|---|---|---|---|
| A | Water Dem | AQUA; | Ad 100 | Ad 100 | Ad 100 |
| A | Keltrol CG-T | XANTHAN GUM; | 0.25 | 0.25 | 0.25 |
| A | 1,3 Butylene Glycol cos grade | BUTYLENE GLYCOL; | 3.00 | 3.00 | 3.00 |
| A | Edeta BD | DISODIUM EDTA; | 0.10 | 0.10 | 0.10 |
| B | AMPHISOL ® K | POTASSIUM CETYL PHOSPHATE; | 2.50 | 2.50 | 2.50 |
| B | Lanette 18 | STEARYL ALCOHOL; | 2.50 | 2.50 | 2.50 |
| B | Finsolv TN | C12-15 ALKYL BENZOATE; | 15.00 | 15.00 | 15.00 |
| B | Cetiol CC | DICAPRYLYL CARBONATE; | 10.00 | 5.00 | 8.00 |
| B | Cetiol B | DIBUTYL ADIPATE; | 3.00 | 3.00 | 3.00 |
| B | PARSOL ® Shield | BIS-ETHYLHEXYLOXYPHENOL METHOXYPHENYL TRIAZINE | 3.00 | 3.00 | |
| B | PARSOL ® TX | TITANIUM DIOXIDE; SILICA; DIMETHICONE | 5.00 | 5.00 | 5.00 |
| B | Hallbrite BHB | BUTYLOCTYL SALICYLATE | | 5.00 | 5.00 |
| B | Euxyl PE 9010 | PHENOXYETHANOL; ETHYLHEXYLGLYCERIN; | 1.00 | 1.00 | 1.00 |

TABLE 2-continued

| Phase | trade name | INCI | Ref 2.1 | Inv-2.1 2 | Ref.2.2 |
|---|---|---|---|---|---|
| B | Sepinov EMT 10 | HYDROXYETHYL ACRYLATE/SODIUM ACRYLOYLDIMETHYL TAURATE COPOLYMER; | 0.40 | 0.40 | 0.40 |
| | | SPF (calculated*) | 16.9 | 21.2 | 12.4 |
| | | L value (average 9 spots) | 34.7 | 33.6 | 39.0 |

*DSM sunscreen optimizer

As can be retrieved from table 2, the combination of BEMT, BHB and a TiO$_2$ micropigment according to the present invention leads to a significant reduction of the L value, reflecting the decreased whitening effect of the composition.

3. EXAMPLE 3

The formulations (O/W emulsions) as outlined in table 3 have been prepared according to standard methods in the art. Then the whitening on LENETA black cards has been tested according to the method as outlined below:

Apply 300 mg of cream on LENETA black card (3 cards are used for each formulation)

cream is spread by a spreading device (speed: 10 mm/s) using a 60 mm spreading knife for homogenous film thickness LAB is measured by Minolta Chroma Meter CR-300, 3 measuring spots on each card average L value is calculated and compared

TABLE 3

| Phase | trade name | INCI | Ref-3.1 | Inv-3.1 | Ref-3.2 |
|---|---|---|---|---|---|
| A | Lanette ® O | cetearyl alcohol; | 1.50 | 1.50 | 1.50 |
| A | Sepigel 305 | polyacrylamide; c13-14 isoparaffin; laureth-7; | 0.25 | 0.25 | 0.25 |
| A | Cremophor A25 | ceteareth-25; | 1.50 | 1.50 | 1.50 |
| A | Lanette 22 | behenyl alcohol; | 2.00 | 2.00 | 2.00 |
| A | Finsolv TN | c12-15 alkyl benzoate; | 13.00 | 8.00 | 11.00 |
| A | Euxyl PE 9010 | phenoxyethanol; ethylhexylglycerin; | 1.00 | 1.00 | 1.00 |
| A | X-Tend 226 | phenethyl benzoate; | 5.00 | 5.00 | 5.00 |
| A | Emulgade A 6 | ceteareth-6; stearyl alcohol; | 2.00 | 2.00 | 2.00 |
| A | PARSOL ® Shield | bis-ethylhexyloxyphenol methoxyphenyl triazine | 3.00 | 3.00 | |
| A | Hallbrite BHB | BUTYLOCTYL SALICYLATE | | 5.00 | 5.00 |
| B | Parsol ® ZX | zinc oxide; triethoxycaprylylsilane; | 15.00 | 15.00 | 15.00 |
| C | Edeta BD | disodium edta; | 0.20 | 0.20 | 0.20 |
| C | Keltrol ® CG-T | xanthan gum; | 0.30 | 0.30 | 0.30 |
| C | 1,3-Butylenglycol | butylene glycol; | 3.00 | 3.00 | 3.00 |
| C | Water Dem | aqua; | Ad 100 | Ad 100 | Ad 100 |
| | | SPF (calculated*) | 18.2 | 21.6 | 13.0 |
| | | L value (average 9 spots) | 40.2 | 35.5 | 40.3 |

*DSM sunscreen optimizer

As can be retrieved from table 3 the combination of BEMT, BHB and a ZnO micropigment according to the present invention leads to a significant reduction of the L value, reflecting the decreased whitening effect of the composition

The invention claimed is:

1. A topical composition comprising, based on total weight of the composition:
   (i) 0.4 to 10 wt.-% of bis-ethylhexyloxyphenol methoxyphenyl triazine,
   (ii) 0.5 to 25 wt.-% of at least one inorganic UV-filter selected from the group consisting of titanium dioxide and zinc oxide, and (iii) an amount of 0.5 to 10 wt.-% of butyloctyl salicylate effective to reduce the whitening effect of the topical composition due to the presence of the at least one UV-filter as determined by a lower L value as compared to a topical composition comprising the bis-ethylhexyloxyphenol methoxyphenyl triazine and the at least one UV-filter but not comprising the butyloctyl salicylate, wherein the topical composition has a sun protection factor (SPF) of at least 18.2 with the proviso that the composition does not comprise isoamyl p-methoxycinnamate, diethylamino hydroxybenzoyl hexyl benzoate and ethylhexyl 2-cyano-octocrylene.

2. The topical composition according to claim 1, wherein the bis ethylhexyloxyphenol methoxyphenyl triazine is present in an amount of 0.8 to 5 wt.-%, based on the total weight of the topical composition.

3. The topical composition according to claim 1, wherein the butyloctyl salicylate is present in an amount of 1 to 8 wt.-%, based on the total weight of the topical composition.

4. The topical composition according to claim 1, wherein the the inorganic UV-filter is present in an amount of 1 to 20 wt.-%, based on the total weight of the composition.

5. The topical composition according to claim 1, wherein the inorganic UV-filter is surface coated.

6. The topical composition according to claim 1, wherein the inorganic UV-filter is selected from the group consisting of double coated titanium dioxide having an inner silica coating and an outer dimethicone coating, zinc oxide coated with triethoxycaprylylsilane and mixtures thereof.

7. The topical compositions according to claim 1, wherein the topical composition is an oil-in-water (O/W) emulsion comprising an oily phase dispersed in an aqueous phase in the presence of an O/W emulsifier.

8. The topical composition according to claim 1, wherein the topical composition further comprises at least one oil selected from the group consisting of butylene glycol, dicaprylate/dicaprate, phenethyl benzoate, $C_{12}$-$C_{15}$ alkyl benzoate, dibutyl adipate, diisopropyl sebacates, dicaprylyl carbonate, di-$C_{12-13}$ alkyl tartrates, diethylhexyl syringylidene malonates, hydrogenated castor oil dimerates, triheptanoin, $C_{12-13}$ alkyl lactates, $C_{16-17}$ alkyl benzoates, propylheptyl caprylates, caprylic/capric triglycerides, diethylhexyl 2,6-naphthalates, octyldodecanol, ethylhexyl cocoates and dibutyl adipate.

9. The topical composition according to claim 1, wherein the topical composition comprises at least one preservative and/or preservative booster selected from the group consisting of ethanol, p hydroxyacetophenone, phenoxyethanol and ethylhexylglycerin.

10. The topical composition according to claim 1, wherein the topical composition further comprises at least one further component selected from the group consisting of xanthan gum, crosslinked acrylate/$C_{10}$-$C_{30}$ alkyl acrylate polymer and hydroxyethyl acrylate/sodium acryloyldimethyl taurate copolymer.

11. The topical composition according to claim 1, wherein the topical composition further comprises at least one co-surfactant selected from the group consisting of cetyl alcohol, cetearyl alcohol, stearyl alcohol and glyceryl stearate.

12. The topical composition according to claim 1, wherein the topical composition at least one alkanediol selected if the preparation comprises from the group consisting of 1,2 pentanediol, 1,2-hexanediol, 1,2-octanediol, 1,2-decanediol, propanediol, propylene glycol and 2-methyl-1,3-propanediol.

13. The topical composition according to claim 1, wherein the the SPF of the topical composition is at least 20.

14. The topical composition according to claim 1, wherein the SPF of the topical composition is at least 20.

15. The topical composition according to claim 1, wherein the bis ethylhexyloxyphenol methoxyphenyl triazine is present in an amount of 1 to 5 wt.-%, based on the total weight of the topical composition.

16. The topical composition according to claim 1, wherein the butyloctyl salicylate is present in an amount of 2 to 6 wt. %, based on the total weight of the topical composition.

17. The topical composition according to claim 1, wherein the inorganic UV-filter is present in an amount of 2 to 15 wt.-%, based on the total weight of the composition.

18. The topical composition according to claim 7, wherein the O/W emulsifier is a cetyl phosphate.

19. The topical composition according to claim 18, wherein the O/W emulsifier is potassium cetyl phosphate.

20. A method of reducing the whitening effect caused by an inorganic UV-filter selected from titanium dioxide and/or zinc oxide when applied to a surface in a topical composition comprising bis-ethylhexyloxyphenol methoxyphenyl triazine and the inorganic UV-filter, wherein the method comprises the step of adding to the topical composition an effective amount of 0.5 to 10 wt.-%, based on the total weight of the topical composition, of butyloctyl salicylate sufficient to reduce the whitening effect of the topical composition due to the presence of the at least one UV-filter as determined by a lower L value as compared to an identical topical composition not comprising the bis-ethylhexyloxyphenol methoxyphenyl triazine and the at least one UV-filter but not comprising the butyloctyl salicylate.

\* \* \* \* \*